United States Patent [19]

Stolowitz et al.

[11] Patent Number: 4,861,726
[45] Date of Patent: Aug. 29, 1989

[54] METHOD OF THIOACYLATION PEPTIDE SEQUENCING WITH ACYLATION OF TRIAZOLINONES

[75] Inventors: Mark L. Stolowitz; Vyas M. Dixit, both of Long Beach; Edward A. Kesicki, San Pedro, all of Calif.

[73] Assignee: Bio-Affinity Systems, Inc., Torrance, Calif.

[21] Appl. No.: 166,420

[22] Filed: Mar. 10, 1988

[51] Int. Cl.[4] .................. G01N 21/64; G01N 33/68
[52] U.S. Cl. ........................................ 436/89; 436/92
[58] Field of Search .................. 436/89, 92, 161, 172

[56] References Cited

U.S. PATENT DOCUMENTS

| | | | |
|---|---|---|---|
| 3,975,155 | 8/1976 | Geyer | 436/92 X |
| 4,065,412 | 12/1977 | Dreyer | 436/89 X |
| 4,110,378 | 8/1978 | Geyer | 436/92 X |
| 4,548,904 | 10/1985 | Kent et al. | 436/89 |
| 4,652,530 | 3/1987 | Rothman et al. | 436/92 |

FOREIGN PATENT DOCUMENTS 0110955  8/1980  Japan ................................ 436/89

OTHER PUBLICATIONS

Previero et al., Chemical Abstracts, vol. 84, No. 21, Abstract No. 147268m, 5/24/76.
Tsugita et al., Chemical Abstracts, vol. 106, No. 11, Abstract No. 81238r, 3/16/1987.

*Primary Examiner*—Robert J. Hill, Jr.
*Attorney, Agent, or Firm*—Blakely, Sokoloff, Taylor, Zafman

[57] ABSTRACT

A protein micro sequencing method for use in conjunction with the thiocylation degradation of polypeptides and proteins is disclosed. The process involves reaction of the N-terminal amino acid of a polypeptide with an excess of a thioacylating reagent. After sufficient time to insure quantitative coupling and removal of excess reagent, the derivatized polypeptide is subjected to cleavage by acid which affords a 2-substituted-5(4H)-thiazolinone. After removal of excess acid, the thiazolinone is reacted with a small excess of a fluorescent or enhanced ultraviolet absorbance reagent having a reactive carboxylic acid chloride, sulfonic acid chloride, chloroformate, isocyanate or anhydride functionality, in the presence of a tertiary amine catalyst, to yield the corresponding 5-O-acyl-2-(substituted)thiazole derivative, detectible by enhanced ultravoilet absorobance or fluorescence emission at extremely low concentration thereby providing a method of sequencing very small amounts of protein.

13 Claims, No Drawings

METHOD OF THIOACYLATION PEPTIDE SEQUENCING WITH ACYLATION OF TRIAZOLINONES

FIELD OF THE INVENTION

The invention relates to sequencing a polypeptide or protein molecule in order to determine its amino acid sequence. More particularly, this invention relates to a novel method for the micro sequencing of very small amounts of protein.

BACKGROUND OF THE INVENTION

Proteins and polypeptides are naturally occuring, and recently, synthetically prepared compounds that are composed of long chains of amino acids. Proteins are found throughout living things and function as enzymes, hormones, immunoglobulins, structural elements, and other consituents of living things. Research regarding the structure and function of a protein often requires that the amino acid sequence (primary structure) of the protein be determined. In order for a protein or the polypeptide constituents thereof to be synthesized, the sequence of amino acids must be determined. In the search involving the function of proteins, the primary structure must first be determined in an attempt to elucidate the mechanism of action of the protein. In recombinant DNA methodology, the primary structure must be determined to elucidate the corresponding structure of a DNA or RNA encoding the same.

The sequence of amino acids in proteins or polypeptides is commonly determined by stepwise chemical degradation in which single amino acids are derivatized and removed one by one from the end of the polypeptide to be identified. The standard method, the Edman degradation, is the preferred method. Alternatively, thioacylation has attracted considerable attention as an effective alternative to the Edman degradation, owing to the particularly mild conditions under which it is employed. However, neither of these methods has proven entirely successful in the micro sequencing of small amounts of protein.

Many physiologically active proteins are present in organisms at such extremely small concentrations that only very small amounts of the proteins can be obtained for sequencing analysis. Most current chemical sequencing methods are done with an amount of protein in the 5–100 nanomole ($5 \times 10^{-9}$ to $10^{-8}$ mole) range. It has been reported that micro sequencing of polypeptides by reverse phase high pressure liquid chromatographic analysis of the degradation products detected by ultraviolet light has been accomplished with protein samples in the range of 50–500 picomoles ($5 \times 10^{-11}$ to $10^{-10}$ mole). Other methods used in the micro sequencing of polypeptides involve radio labeling of the polypeptide or reagent, intrinsic radio labeling of the protein, and enhanced ultraviolet detection of sequence degradation products, and others. However, each of the foregoing prior art methods have limitations and restrictions which are recognized in the literature. They have not been used with overall satisfactory results. Currently, the best prior art method of micro sequencing is computer aided ultraviolet detection of gas phase microsequencer degradation products separated by microbore high pressure liquid chromatography.

Many techniques have been developed in recent years for the analytical separation of proteins or polypeptides exhibiting physiological activity when present in very low quantities of about 1 picomole ($10^{-12}$ mole), which is about 50 nanograms of a 50,000 molecular weight protein. One such detection method which has inherent sensitivity in the femtomole ($10^{-15}$ to $10^{-13}$ mole) range is fluorescence. The use of fluorescence detection in sequencing is described below.

THIOACYLATION

The thioacylation degradation of proteins and polypeptides was first proposed by Barrett (Barrett, G. C., Chem. Comm., (1967) 487) as an alternative to the Edman degradation (Edman, P., Acta Chem. Scand., (1950) 4, 283). The process involves reacting the N-terminal amino acid of a starting polypeptide immobilized on an insoluble support (heterogeneous phase reaction) with a thioacylating reagent in an alkaline aqueous or anhydrous solvent. The excess reagent is removed by the washing of the immobilized polypeptide, and by-products of the reaction resulting from the decomposition of the reagent are similarly removed, to yield the N-thioacyl polypeptide, Formula I, wherein X is an alkyl, aryl or aryl-alkyl substituent, R represents the various amino acid side chains and -(peptide) is the starting peptide immobilized on a solid support and not including the N-terminal amino acid.

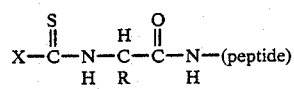

Formula I

In the second step, the thioacyl polypeptide is subjected to cleavage by volatile anhydrous acid to afford the 2-substituted-5(4H)-thiazolinone of the N-terminal amino acid, Formula II. Thioacylation offers some advantages over the Edman degradation in that the cleavage reaction is short in duration and occurs under relatively mild conditions. Also liberated during the cleavage reaction is the salt of the residual polypeptide, which is the starting polypeptide with the N-terminal amino acid removed.

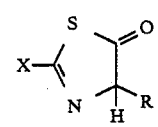

Formula II

2-Methyl-5(4H)-thiazolinones were historically identified through the regeneration of the free amino acids by hydrolysis (Mross, Jr., G. A., (1971) Ph.D. Dissertation, University of California, San Diego). Consequently, serine, threonine and tryptophan were not recovered in high yield as a result of their instability during hydrolysis. Alternatively, 2-methyl-5(4H)-thiazolinones have been identified by gas liquid chromaotgraphy, preferably, after reaction with excess acetic anhydride in pyridine or acetyl chloride in TFA (Simpson, D. L., Hranisewljevic, J. and Davidson, E. A., Biochemistry, (1972) 11, 1849) which yields the corresponding 5-O-acetyl-2-methylthiazoles, Formula III.

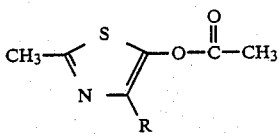

Formula III

2-Phenyl-5(4H)-thiazolinones have been identified directly by mass spectrometry and by thin layer chromatography after conversion to the corresponding N-thiobenzoyl amino acid anilides (Barrett, G. C. and Khokhar, A. R., *J. Chromatog.*, (1969) 39, 47).

Various carbodithioic esters, thiono esters and thiono imides including carboxymethyl dithiobenzoate, cyanomethyl dithiobenzoate, m-nitrobenzoylthionocholine, N-thiobenzoylsuccinimide, thioacetyl thioglycolic acid and methyl dithioacetate have been employed as reagents for the sequential degradation of polypeptides. The aforementioned compounds are not particularly good thioacylating reagents and this constituted an important drawback for the development of a satisfactory procedure for sequential analysis. Aminolysis of carbodithioic esters is susceptible to general base catalysis and experimental conditions by which simple alkyl esters of aliphatic dithioacids (methyl dithioacetate) behave as satisfactory thioacylating reagents have been reported (Previero, A., Gourdol, A., Derancourt, J. and Coletti-Previero, M.-A., *FEBS Lett.*, (1975) 51, 68). Thioacylating reagents exhibit low solubility in aqueous media which limits their use in homogeneous phase techniques. This limitation was overcome by the advent of solid phase and pulsed liquid methods.

FLUORESCENT ISOTHIOCYANATES

In addition to phenylisothiocyanate (PITC), several other aromatic isothiocyanates have been prepared for use in micro sequencing by the Edman degradation. 4-N-Dimethylaminonaphthaleneisothiocyanate (DNTC), 4-N-dimethylaminoazobenzene-4'-isothiocyanate (DABITC) and fluorescein isothiocyanate have been utilized in protein and polypeptide sequencing. DABITC has been a particularly useful reagent for liquid and solid phase sequencing and has afforded a more sensitive sequential analysis (by detection in the visible region of the spectrum) than the other isothiocyanate homologues. Recently, 4-(N-1-dimethylaminonaphthalene-5-sulfonylamino)phenylisothiocyanate (DNSA-PITC) has attracted attention as a potentially useful micro sequencing reagent (Hirano, H. and Wittmann-Liebold, B., *Biol. Chem. Hoppe-Seyler*, (1986) 367, 1259).

Quantitative coupling of fluoresecent isothiocyanates has been demonstrated only in homogeneous phase reactions at elevated temperature. To overcome this inadequacy a double coupling method (Chang, J. Y., Brauer, D. and Wittmann-Liebold, B., *FEBS Lett.*, (1978) 93, 205) was developed in which reaction of the fluorescent isothiocyanate is followed by a second reaction with PITC to achieve quantitative coupling. The limited coupling efficiency of fluorescent isothiocyanates in heterogeneous phase reactions results from steric considerations. Attempts to employ fluorescent aliphatic isothiocyanates, to overcome this problem, resulted in reagents which lack sufficient reactivity for satisfactory use in the Edman degradation (Salnikow, J., Palacz, Z. and Wittmann-Liebold, B., in *Methods in Protein Sequence Analysis*, Walsh, K. A., Ed., Humana Press, Clifton, NJ (1987), 247–260).

A further complication encountered with the preparation of fluorescent isothiocyanates in that incorporation of the isothiocyanate moiety directly into the aromatic system responsible for the desired properties of fluorescence has been shown to result in several instances in a dramatic reduction of fluorescence of the resulting reagent rendering the reagent unsuitable. For example, the isothiocyanate and valine thiohydantoin prepared from 2-(4-aminophenyl)-6-methylbenzthiaole, a highly fluorescent compound, exhibits only a residual 1–2% of the fluorescence of the parent compound (Salnikow, J., et al., ibid.). Consequently, if the fluorescence properties of a given compound are to be preserved, the entire phenylisothiocyanate moeity must be appended to the compound, as for example, in DNSAPITC. This necessarily results in bulky reagents suitable only for use in conjunction with doulbe coupling methods.

An alternative approach to the preparation of fluorescent derivatives is described in U.S. Pat. No. 4,548,904. PITC is substituted in the 4-position of the phenyl ring with an alkylamine moiety bearing an acid-labile protecting group as in 4-(N-t-butoxycarbonylaminomethyl)phenylisothiocyanate (BAMPITC). A primary alkylamine, available for subsequent reaction with a fluorescent tag, was thought to be generated during the acid cleavage step of the Edman degradation. However, it has been reported that 4-N-t-butoxycarbonylaminomethyl-substituted PTC peptides unexpectedly eliminate methylamine during the cleavage reaction with anhydrous trifluoroacetic acid (Shan-Wei, J., Gui-Xiang, C., Zbigniew, P. and Wittmann-Liebold, B., *FEBS Lett.*, (1986) 198, 150). Consequently, BAMPITC cannot be employed in Edman degradations as previously reported (L'Italien, J. J. and Kent, S. B. H., *J. Chromatog.*, (1984) 283, 149).

A similar approach involving a base-labile protecting group, as in 4-(N-trifluoroacetamidoethyl)phenylisothioacyanate, has been suggested (Hood, L., et al, in Methods in Protein Sequence Analysis, Walsh, K. A., Ed., Humana Press, Clifton, NJ (1987), 21–41). In this approach the reagent is first coupled to an immobilized peptide and the protecting group subsequently removed. The phenylthiocarbamyl polypeptide bearing the N-terminal alkylamine moiety is then reacted with a fluorescent tag prior to the cleavage reaction.

As indicated herein, attempts have been made to use fluorescent isothiocyanes in the Edman degradation. However, overall success in the sequencing of very small amounts of protein has not been demonstrated to date. Accordingly a substantial need exists for a method adapted for the sequencing of amounts of protein in the low picomole to sub-picomole range.

SUMMARY OF THE INVENTION

A novel protein micor sequencing method for use in conjunction with the thioacylation degradation of polypeptides and proteins is disclosed. The process involves reaction of the N-terminal amino acid of a polypeptide with an excess of a thioacylating reagent. After sufficient time to insure quantitative coupling and removal of excess reagent, the derivatized polypeptide is subjected to cleavage by acid which affords a 2-substituted-5(4H)-thiazolinone. After removal of excess acid, the thiazolinone is reacted with a small excess of a fluorescent or enhanced ultraviolet absorbance reagent having a reactive carboxylic acid chloride, sulfonic acid chloride, chloroformate, isocyanate or anhydride functionality, in the presence of a tertiary amine catalyst, to yield the corresponding 5-O-acyl-2-(substituted)-thiazole derivative, detectible by enhanced ultraviolet absorbance or fluorescence emission at extremely low concentration thereby providing a method of sequencing very small amounts of protein.

It is an object of this invention to provide a peptide sequencing system capable of sequencing small amounts of proteins or polypeptides.

It is another object of this invention to provide a peptide sequencing system capable of detection of sequencing products in the femtomole range.

It is yet another object of this invention is to provide a peptide sequencing system wherein there is quantitative incorporation of a fluorescent moeity into the compound to be detected.

DETAILED DISCUSSION

The present invention relates to a novel method for use in conjunction with the thioacylation degradation of polypeptides to determine the primary structure of very small amounts of protein. The process first involves reaction of the N-terminal amino acid of a starting polypeptide immobilized on an insoluble support (heterogeneous phase reaction) with an excess of a thioacylating reagent having a reactive functionality of the form —C(S)W, where W is a leaving group, such as —SR′, —OR′, or —NR′R″ with R′ and R″ being alkyl, aryl, acyl, or substituted derivatives thereof. Examples of thioacylation reagents include S-thiobenzoylmercaptoacetic acid, thioacetylthioglycholic acid and methyl dithioacetate. The reaction occurs in the presence of an acid scavenger in alkaline aqueous or anhydrous solvent, at room temperature or at elevated temperature. After sufficient time to ensure thioacylation of the polypeptide, for a few minutes up to several hours and generally 15 to 45 minutes, the excess reagent is removed by washing of an immobilized polypeptide, and by-products of the reaction resulting from the decomposition of the reagent are similarly removed, to yield a thioacyl polypeptide of general formula IV wherein X is an alkyl, aryl or aryl-alkyl substituent, and is preferably methyl, R represents the various amino acid side chains and -(peptide) represents the remainder of the starting peptide, not including the N-terminal amino acid.

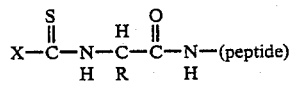

Formula IV

The compound of general formula IV is next subjected to cleavage by reaction with a volatile anhydrous perfluorinated carboxylic acid, preferably trifluoroacetic acid (TFA), at room temperature or at elevated temperature, to yield the 2-substituted-5(4H)-thiazolinone of general formula V. Also liberated during the cleavage reaction is the salt of the residual polypeptide, which is the starting polypeptide with the N-terminal amino acid removed.

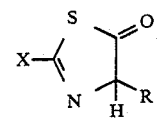

Formula V

After separation from the salt of the residual polypeptide and removal of excess acid in vacuo or by evaporation under a stream of nitrogen gas at elevated temperature, the compound of general formula V is next reacted with a small excess of a fluroescent carboxylic acid chloride, sulfonic acid chloride, chloroformate, isocyanate or anhydride, in the presence of a tertiary amine catalyst such as triethylamine, pryidine, or diisopropylethylamine, in an aprotic organic solvent, at room temperature, to yield the corresponding 5-O-acyl-2-(substituted)thiazole of general formula VI wherein Y is either —C(O)—, —SO$_2$—, —C(O)O— or —C(O)NH— and Z is a substituent containing a moeity which exhibits enhanced ultraviolet absorption or fluorescence emission properties detectable at extremely low concentration as required in the sequencing of very small amounts of protein. The process described above is then repeated for each N-terminal amino acid in the polypeptide, until the entire polypeptide is sequenced.

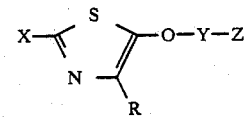

Formula VI

Preferred fluorescent or enhanced ultraviolet absorbance reagents used in the acylation of the thiazolinone include 3,5-dinitrobenzoylchloride, 5-N,N-dimethylaminonaphthalenesulfonyl chloride, 4-(dimethylamino)azobenzene-4′-sulfonyl chloride, 9-fluorenylmethylchloroformate and 7-[(chlorocarbonyl)methoxy]-4-methylcoumarin.

The thiazole derivatives which result from the afore-described process are ordinarily subjected to chromatographic analysis, most commonly reverse phase high pressure liquid chromatography (HPLC). The compounds may be detected by ultraviolet absorbance or fluorescence emission or both in the same analysis. Standard methods, equipment, solvents, buffers, reaction sequences of manual and automatic sequencing can be used with minor modifications where necessary to accomodate the reaction of the 2-alkyl-5(4H)-thiazolinone or 2-aryl-5(4H)-thiazolinone with the carboxylic acid chloride, sulfonic acid chloride, chloroformate, isocyanate or anhydride. Preferred automated methods of sequencing include the spinning cup, solid phase, pulsed liquid and gas phase methods. Adjustment of chromatographic mobile phase constituents as well as excitation and emission wavelengths may be necessary to optimize sensitivity by fluorescence detection. The following examples describe the preparation of chromatographic standards and the use of the process in the sequencing of peptides.

EXAMPLE I

Preparation of 5-O-[7-(Carbonylmethoxy)4-methylcoumarin]-2-methylthiazole Standards Solutions of methyl dithioacetate (5 mmole) in tetrahydrofuran (20 mL) and of amino acid (5 mmole) in 1N sodium hydroxide (10 mL) were mixed, and the mixture was shaken vigorously for one minute. Additional equivalents of sodium hydroxide solution were added where amino acids were used as their hydrochloride salts or contained acidic side chain functionalities (lysine, histidine, aspartic acid, glutamic acid and tyrosine). The mixture was shaken at room temperature for 12 hours, the change toward pale yellow in color indicating the progress of the reaction. Excess reagent and byproducts were removed by extraction into hexane. The solutions were then acidified with 2N sulfuric acid and extracted with several portions of ethyl acetate. The extracts were combined, dried over MgSO4 after through washing with water, and evaporated in vacuo to afford the N-thioacetyl amino acids in approximately 80% yield.

2-Methyl-5(4H)-thiazolinones were prepared by cyclization of N-thioacetyl amino acids with dicyclohexylcarbodiimide. Solutions in dichloromethane of dicyclohexylcarbodiimide (1 mmole, 5 mL) and N-thioacetyl amino acids (1 mmole, 5 mL) were mixed. Dicyclohexylurea started to precipitate from the resulting solution within a few seconds. The mixture was filtered and the filtrate and washings concentrated under reduced pressure to 10 mL. The mixture was then allowed to stand on ice for 30 min; then filtered again to afford a quantitative recovery of dicyclohexylurea.

7-[(Chlorocarbonyl)methoxy]-4-methylcoumarin was prepared from 7-hydroxy-4-methylcoumarin as previously described (Karlsson, K.-E., Wiesler, D., Alasandro, M. and Novotny, M., *Anal. Chem.*, (1985) 57 229). To each of the 2-methyl-5(4H)-thiazolinones (1 mmole) in dichloromethane (10 mL), cooled on ice, was added 7-[(chlorocarbonyl)methoxy]-4-methylcoumarin (1.1 mmole) and triethylamine (1 mL) and the resulting solutions were agitated for one minute then evaporated under reduced pressure to afford a quantitative yield of the 5-O-[7-(carbonylmethoxy)4-methylcoumarin]-2-methylthiazole standards. The standards were taken up in chloroform and purified by chromatography on silica gel.

EXAMPLE II

Thioacetylation Degradation

The peptide Fmoc-Ala-Phe-Gly-Ile-Ala-OH (3 mg) was immobilized on N-(2-aminoethyl)-3-aminopropyl glass (15 mg, 75 angstrom pore, 200–400 mesh) by activation with diisopropylcarbodiimide in N,N-dimethylformamide (DMF). The Fmoc group was subsequently removed by reaction with 20%(v/v) piperidine in DMF. Thioacetylthioglycolic acid (TATG) was synthesized as previously reported (Jensen, K. A. and Pedersen, C., *Acta Chem. Scand.*, (1961) 15, 1087).

The immobilized peptide was sequenced manually by thioacetylation degradation as follows; TATG (1.0 gram) was dissolved in 25 mL of anhydrous pyridine, and 1.2 mL of triethylamine (TEA) were added. An aliquot of the solution was removed and mixed with an equal volume of water, and the pH adjusted to approximately 9.6 by the addition of TEA. The peptide was deposited in a 5 mL glass fritted reaction vessel with a water jacket that was maintained at 42° C. The peptide was treated with 1.5 mL of TATG stock solution and incubated with constant agitation for 30 min. Excess TATG and various byproducts were removed by a series of washes, including 50% pyridine, water, and methanol; each wash involved 3–4 mL of solvent. The methanol washed beads are dried by a stream of nitrogen for a period of 10 min. The 2-methyl-5(4H)-thiazolinone was then liberated by treatment of the beads with 1.5 mL of trifluoroacetic acid for 3 minutes. After collection of the thiazolinone, the beads were washed twice with methanol and then dried under a stream of nitrogen prior to initiating the next cycle of degradation.

The 2-methyl-5(4H)-thiazolinone fractions were concentrated by evaporation under at stream of nitrogen gas at 50° C. The residue was dissolved in 500 uL of dichloromethane containing 7-[(chlorocarbonyl)methoxy]-4-methylcoumarin (1.2 nmoles). The derivatization was catalyzed by the addition of 50 uL of TEA and the samples were allowed to stand for 3 minutes; then concentrated by evaporation under a stream of nitrogen gas at 50° C.

EXAMPLE III

Analysis and Detection

The 5-O-[7-(carbonylmethoxy)4-methylcoumarin]-2-methylthiazoles were separated by gradient elution HPLC on an IBM Instruments 5u, 4.6 mm×150 mm, C18 column. The HPLC system was comprised of an IBM 9560 Ternary Gradient Liquid Chromatograph and an IBM 9505 Automatic Sample Handler. Sample volumes of 20 uL were utilized. The fluorescence detector was a Kratos 980 with a 5 uL flow cell. The excitation wavelength was 315 nm and a 390 nm cutoff filter was used for emission measurements. The mobile phase was prepared by the addition of 10.0 mL of acetic acid, 4.0 mL of TEA and 2.0 mL of TFA to one liter of water. The pH of the mobile phase was adjusted to 3.1. The flow rate was 1.5 mL/min. Samples were injected in acetonitrile and gradient elution was accomplished by the adition of acetonitrile (up to 70%) to the mobile phase.

We claim:

1. A method for determining the identity of an N-terminal amino acid of a polypeptide comprising the steps of:
   (a) providing a starting polypeptide having an N-terminal amino acid;
   (b) reacting said polypeptide with a thioacylating reagent having a reactive functionality of the form —C(S)W where W is a leaving group, to form a compound having the formula IV, wherein X is H, alkyl, aryl or aryl-alkyl, R represents an amino acid side chain and -(peptide) represents the starting peptide, not including the N-terminal amino acid;

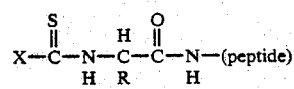

(c) cleaving the compound of formula IV with a volatile anhydrous acid to form a residual polypeptide, which comprises the starting polypeptide with the N-terminal amino acid removed, and a 2-substituted-5(4H)-thiazolinone compound of general formula V;

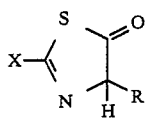

(d) reacting the compound of general formula V with a fluorescent reagent with a reactive functionality selected from the group consisting of carboxylic acid chloride, sulfonic acid chloride, chloroformate, isocyanate and anhydride, in the presence of a tertiary amine catalyst, to yield a corresponding 5-O-acyl-2-(substituted)thiazole of general formula VI wherein Y is selected from the group consisting of —C(O)—, —SO$_2$—, —C(O)O— or —C(O)NH— and Z is a substituent containing a moiety which exhibits enhanced ultraviolet absorption or fluorescence emission properties detectable at extremely low concentration;

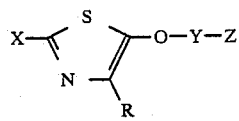

(e) identifying the 5-O-acyl-2-(substituted)thiazole of general formula VI.

2. The method of claim 1 wherein said polypeptide is immobilized on a solid support prior to step b.

3. The method of claim 1 wherein said reactive functionality is selected from the group consisting of —C(S)SR', —C(S)OR' and C(S)NR'R" wherein R' and R" are alkyl, aryl, acyl or substituted derivatives thereof.

4. The method of claim 3 wherein said thioacylating reagent is selected from the group consisting of thioacetylthioglycholic acid and methyl dithioacetate.

5. The method of claim 1 wherein step b occurs in the presence of excess thioacylating reagent.

6. The method of claim 5 further comprising removing excess thioacylating reagent prior to step c.

7. The method of claim 1 wherein step b occurs in the presence of an acid scavenger in an alkaline aqueous solvent or an anhydrous solvent.

8. The method of claim 1 wherein said volatile anhydrous acid is trifluoroacetic acid.

9. The method of claim 1 further comprising separating the compound of formula V from said residual polypeptide and separating said acid from said compound of formula V.

10. The method of claim 1 wherein said fluorescent reagent is selected from the group consisting of 3,5-dinitrobenzoylchloride, 5-N,N-dimethylaminonaphthalenesulfonyl chloride, 4-(dimethylamino)azobenzene-4'-sulfonyl chloride, 9-fluorenylmethylchloroformate and 7-[(chlorocarbonyl)methoxy]-4-methylcoumarin.

11. The method of claim 10 wherein said fluorescent reagent is 7-[(chlorocarbonyl)methoxy]-4-methylcoumarin.

12. The method of claim 1 wherein said fluorescent reagent is an acid chloride.

13. The method of claim 1 wherein said tertiary amine catalyst is selected from the group consisting of triethylamine, pyridine and diisopropylethylamine.

* * * * *